United States Patent [19]

Vrckovnik et al.

[11] Patent Number: 5,602,224
[45] Date of Patent: Feb. 11, 1997

[54] SILICONE ALKYL QUATS

[75] Inventors: Richard O. Vrckovnik, Toronto, Canada; Anthony J. O'Lenick, Jr., Lilburn, Ga.

[73] Assignee: Siltech Inc., Norcross, Ga.

[21] Appl. No.: 617,571

[22] Filed: Mar. 19, 1996

[51] Int. Cl.$^6$ .................................................. C08G 77/06
[52] U.S. Cl. .................. 528/21; 528/34; 556/425; 556/469
[58] Field of Search ................. 528/21, 34; 556/425, 556/469

[56] References Cited

U.S. PATENT DOCUMENTS

| | | |
|---|---|---|
| 4,602,078 | 7/1986 | Joseph et al. ........................... 528/34 |
| 5,378,787 | 1/1995 | Vrckovnik . |
| 5,502,146 | 3/1996 | Inoue et al. ............................. 528/34 |

*Primary Examiner*—Melvyn I. Marquis

[57] ABSTRACT

The invention relates to a series of novel silicone compounds which contain fatty alkyl groups. This class of compounds provides unique solubility in many organic softeners, and increases the effectiveness of the softening of fatty quats. These materials are applied to fibers including textile fibers and hair and skin. The compounds of the present invention contain which contain a fatty substituted quaternary group, a silicone group and a reactive silanol groups. The presence of the positive charge on the nitrogen results in substantivity to many substrates, the presence of a silicone portion results in compatability in silicone fluids and the presence of the fatty tail on the molecule results in fatty solubility. The resulting material is surface active and will allow for the incorporation of silicone into a fatty system or of a fatty quat in a silicone system.

20 Claims, No Drawings

SILICONE ALKYL QUATS

BACKGROUND OF THE INVENTION

1. Field of the Invention

The invention relates to a series of novel silicone reactive compounds which contain fatty alkyl groups. This class of compounds provides unique solubility in many organic softeners, and increases the effectiveness of the softening of fatty quats. These materials are applied to fibers including textile fibers and hair and skin. The compounds of the present invention contain which contain a fatty substituted quaternary group, a silicone group and a reactive silanol groups. The presence of the positive charge on the nitrogen results in substantivity to many substrates, the presence of a silicone portion results in comparability in silicone fluids and the presence of the fatty tail on the molecule results in fatty solubility. The resulting material is surface active and will allow for the incorporation of silicone into a fatty system or of a fatty quat in a silicone system.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low. Silicone compounds give good lubrication to the fiber and a slick softening effect.

Fatty cationic materials have been used as softeners for many years. They are not soluble in silicone fluids. These softeners are more greasy in their hand and do not provide the desired fiber lubrication. Many attempts have been made to prepare blends of silicone fluids and fatty quats to provide the best properties of both materials. Alas, silicone oil and fatty quats are not soluble. The result of admixing silicone fluids with fatty quats is a thick milky mixture, which separates rapidly.

There is therefore a desire to provide a material which allows for the incorporation of silicone oil into fatty quats.

3. Object of the Invention

It is the object of the present invention to provide a series of novel silicone compounds which contain a fatty substituted quaternary group, a silicone group and a reactive silanol groups. The incorporation of the fatty cationic and silicone group into a molecule results in a product which having both a silicone portion and a silicone portion will allow for the solubilization of the two heretofore incompatible materials into a system which is truly multifunctional.

Still other objectives will become clear as the teachings of the invention are read.

SUMMARY OF THE INVENTION

The invention relates to a series of novel silicone compounds which contain in one molecule a fatty substituted quaternary group, a silicone group and a reactive silanol groups.

As will become clear from the disclosure, the compounds of the present invention not only require all of the functional components described above but need them in the correct ration and in the correct three dimensional structure to be effective.

The compounds of the invention are prepared by the following reaction:

(a) a cationic alkoxy silane is reacted with a silanol to produce a cationic alkoxy polymer. The reactants are:

$$R^3 - \overset{R^2}{\underset{R^4}{\overset{|}{N^{\oplus}}}} - (CH_2)_3 - Si - (OR^1)_3 \quad Cl^{\ominus} \quad \text{Alkyl Quat Alkoxy Silane}$$

$R^1$ is methyl or ethyl;

$R^2$ is alkyl having from 6 to 20 carbon atoms;

$R^3$ and $R^4$ are each independently selected from the group consisting of alkyl having from 1 to 20 carbon atoms and $$-(CH_2CH_2O)x-(CH_2CH(CH_3)O)y-(CH_2CH_2O)z-H$$

x, y and z are each independently integers ranging from 0 to 20, with the proviso that x+y+z is greater than 1.

(b) a silanol conforming to the following structure:

$$\text{HO} - \underset{\text{Me}}{\overset{\text{Me}}{\underset{|}{\text{Si}}}} + \text{O} - \underset{\text{Me}}{\overset{\text{Me}}{\underset{|}{\text{Si}}}} -)a - \text{O} - \underset{\text{Me}}{\overset{\text{Me}}{\underset{|}{\text{Si}}}} - \text{OH}$$

a is an integer from 10 to 2000;

Me is methyl.

The simplest form of the reaction involves the reaction of the silanol with the methoxy to give the following structure:

$$R^3 - \overset{R^2}{\underset{R^4}{\overset{|}{N^{\oplus}}}} - (CH_2)_3 - \underset{\text{OMe}}{\overset{\text{OMe}}{\underset{|}{\text{Si}}}} - O - \underset{\text{Me}}{\overset{\text{Me}}{\underset{|}{\text{Si}}}} + O - \underset{\text{Me}}{\overset{\text{Me}}{\underset{|}{\text{Si}}}} -)a - O - \underset{\text{Me}}{\overset{\text{Me}}{\underset{|}{\text{Si}}}} - \text{OH}. \quad Cl^{\ominus}$$

Since there remains a terminal silanol and two methoxy (OMe) groups still to react a polymer is generated which has three dimensionality. This is due to the reaction of the silanol hydroxyl groups with the methoxy groups, and the generation of methanol.

The three dimensionality of this type of reaction is discussed in U.S. Pat. No. 5,378,787 incorporated herein by reference. The reaction of the antino silane and the silanol described in U.S. Pat. No. 5,378,787 occurs without catalyst. The substitution of the alkyl quat for the trimethoxy in the technology of U.S. Pat. No. 5,378,787 will not result in a reaction. We have discovered that there needs to be included in the reaction mixture a catalytic amount of a fatty amine catalyst. Such amine catalysts are selected from momoethanolamine, diethanolamine, triethanolamine, alkyl amine conforming to the following structure:

$$CH_3-(CH_2)b-NH_2$$

b is an integer ranging from 0 to 19; and cyclohexylamine.

The compound of the present invention requires that the ratio of silanol hydroxyl equivalents to silane alkoxy group be less than 1:1. This will result in residual alkoxy groups which will lead to durability. The functional ratio of silanol groups to alkoxy group ranges from 1 silanol to 2–3 alkoxy.

The preferred reactants therefore are;

(a) a cationic alkoxy siloxane conforming to the following structure:

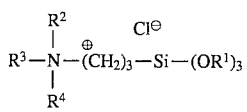

wherein:

$R^1$ is methyl or ethyl;

$R^2$ is alkyl having from 6 to 20 carbon atoms;

$R^3$ and $R^4$ are each independently selected from the group consisting of alkyl having from 1 to 20 carbon atoms and —(CH$_2$CH$_2$O)x—(CH$_2$CH(CH$_3$)O)y—(CH$_2$CH$_2$O)z—H x, y and z are each independently integers ranging from 0 to 20, with the proviso that x+y+z is greater than 1.

(b) a silanol conforming to the following structure:

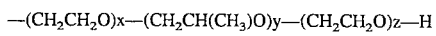

a is an integer from 10 to 2000;

Me is methyl; and (c) an amine catalysts are selected from the group consisting of monoethanolamine, diethanolamine, triethanolamine, alkyl amine conforming to the following structure:

CH$_3$—(CH$_2$)b—NH$_2$ b is an integer ranging from 0 to 19; and cyclohexylamine.

RAW MATERIAL EXAMPLES (A) Silanol Compounds

Silanol compounds are well known and are marketed in the trade under many names. The compounds conform to the following generic structure;

Compounds of the following structure are available from Siltech Inc. Norcross Ga and are marketed under the Siltech S series tradename shown;

| Example | Name | Molecular Weight | x |
|---|---|---|---|
| 1 | Siltech S 701 | 1,000 | 11 |
| 2 | Siltech S 706 | 6,000 | 80 |
| 3 | Siltech S 710 | 10,000 | 133 |
| 4 | Siltech S 750 | 50,000 | 673 |
| 5 | Siltech S 790 | 86,000 | 1160 |

(B) Cationic Silane

Cationic silane compounds are available from several manufacturers.

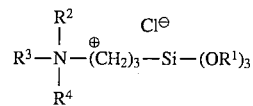

$R^1$ is methyl or ethyl;

$R^2$ is alkyl having from 6 to 20 carbon atoms;

$R^3$ and $R^4$ are each independently selected from the group consisting of alkyl having from 1 to 20 carbon atoms and —(CH$_2$CH$_2$O)x—(CH$_2$CH(CH$_3$)O)y—(CH$_2$CH$_2$O)z—H x, y and z are each independently integers ranging from 0 to 20, with the proviso that x+y+z is greater than 1.

| Example | $R^1$ | $R^2$ | $R^3$ | $R^4$ |
|---|---|---|---|---|
| 6 | Methyl | C$_6$H$_{13}$ | CH$_3$ | CH$_3$ |
| 7 | Ethyl | C$_{12}$H$_{25}$ | C$_6$H$_{13}$ | CH$_3$ |
| 8 | Methyl | C$_{18}$H$_{37}$ | C$_{18}$H$_{37}$ | CH$_3$ |
| 9 | Ethyl | C$_{20}$H$_{41}$ | CH$_3$ | CH$_3$ |
| 10 | Methyl | C$_{18}$H$_{37}$ | C$_{20}$H$_{41}$ | CH$_3$ |

Examples 10–16

$R^3$ and $R^4$ are each:

—(CH$_2$CH$_2$O)x—(CH$_2$CH(CH$_3$)O)y—(CH$_2$CH$_2$O)z—H

| | | | $R^3$ | | | $R^4$ | | |
|---|---|---|---|---|---|---|---|---|
| Example | $R^1$ | $R^2$ | x | y | z | x | y | z |
| 6 | Methyl | C$_6$H$_{13}$ | 0 | 5 | 2 | 0 | 5 | 2 |
| 7 | Ethyl | C$_{12}$H$_{25}$ | 5 | 5 | 5 | 5 | 5 | 5 |
| 8 | Methyl | C$_{18}$H$_{37}$ | 10 | 10 | 2 | 10 | 10 | 2 |
| 9 | Ethyl | C$_{20}$H$_{41}$ | 20 | 20 | 20 | 20 | 20 | 20 |
| 10 | Methyl | C$_{18}$H$_{37}$ | 2 | 2 | 2 | 2 | 2 | 2 |

EXAMPLES

General Conditions

The reaction is conducted using the following general procedure;

To a suitable reaction vessel equipped with mechanical agitation, thermometer, and dean stark trap is added the specified amount of the specified silanol. The agitation is started. Next the specified amount of water is added, along with 0.5% by weight catalyst. Next the specified amount of the specified silane. The reaction mass is heated to 80–85 C. The reaction mass is held at this temperature for 3–5 hours. During that time the reaction mass becomes clear and homogeneous. The product is converted into the final product as shown below.

Solvents like ethanol, methanol or other solvents can be added to lower the viscosity if desired.

| Example | Silanol Example | Grams | Silane Example | Grams | Water Grams |
|---|---|---|---|---|---|
| 24 | 1 | 500.0 | 6 | 133.0 | 54.0 |
| 25 | 2 | 3000.0 | 7 | 242.0 | 54.0 |
| 26 | 3 | 5000.0 | 8 | 372.0 | 54.0 |
| 27 | 4 | 25000.0 | 9 | 188.0 | 54.0 |
| 28 | 5 | 43000.0 | 10 | 254.0 | 54.0 |
| 29 | 5 | 43000.0 | 11 | 326.0 | 54.0 |
| 30 | 4 | 25000.0 | 12 | 575.0 | 54.0 |
| 31 | 3 | 5000.0 | 13 | 813.0 | 54.0 |
| 32 | 2 | 3000.0 | 15 | 2045.0 | 54.0 |
| 33 | 1 | 500.0 | 16 | 267.0 | 54.0 |

Applications Examples

To show the solubilities of the compounds of the present invention, two materials were chosen as solvents, (a) 350 visc. silicone fluid, which is an item of commerce from Siltech Inc. of Norcross Ga., and (b) Stearyl trimethyl ammonium chloride.

Polydimethylsiloxane (PDMS) conforms to the following structure;

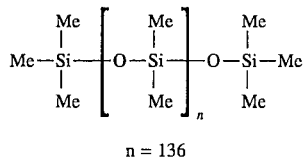

n = 136

Stearyl trimethyl ammonium chloride (STAC) conforms to the following structure:

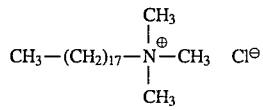

The number of grams of each component were blended in a beaker and heated to 80 C. The agitation was stopped and the clarity observed.

| | A | B | C | D |
|---|---|---|---|---|
| Example 24 | — | 50 | — | — |
| Example 29 | — | — | 50 | — |
| Example 33 | — | — | — | 33 |
| STAC | 50 | 50 | — | 33 |
| PDMS | 50 | — | 50 | 33 |
| Comments | Split | Clear | Clear | Clear |

The above data not only shows the different solubilities achievable using the technology of the present invention, but also shows that the compounds of the present invention can be used to couple the two components which are by themselves not miscible. (Those two components are polydimethylsiloxane and Stearyl trimethyl ammonium chloride).

What is claimed:

1. An silicone polymer made by the reaction of (a) a cationic alkoxy silane conforming to the following structure:

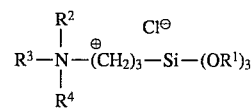

wherein;

$R^1$ is methyl or ethyl;

$R^2$ is alkyl having from 6 to 20 carbon atoms;

$R^3$ and $R^4$ are each independently selected from the group consisting of alkyl having from 1 to 20 carbon atoms and

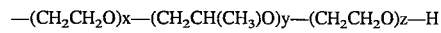

x, y and z are each independently integers ranging from 0 to 20, with the proviso that x+y+z is greater than 1;

(b) a silanol conforming to the following structure:

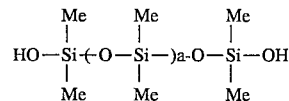

a is an integer from 10 to 2000;

Me is methyl; and (c) an amine catalyst selected from the group consisting of monoethanolamine, diethanolamine, triethanolamine, alkyl amine conforming to the following structure:

$$CH_3-(CH_2)b-NH_2$$

b is an integer ranging from 0 to 19; and cyclohexylamine.

2. A silicone polymer of claim 1 wherein; $R^2$ is alkyl having from 6 to 10 carbon atoms.

3. A silicone polymer of claim 1 wherein;
$R^2$ is alkyl having from 12 to 20 carbon atoms.

4. A silicone polymer of claim 1 wherein;
$R^2$ is alkyl having from 18 to 20 carbon atoms.

5. A silicone polymer of claim 1 wherein;
$R^3$ is alkyl having from 1 to 10 carbon atoms.

6. A silicone polymer of claim 1 wherein;
$R^3$ is alkyl having from 10 to 20 carbon atoms.

7. A silicone polymer of claim 1 wherein;
$R^4$ is alkyl having from 1 to 10 carbon atoms.

8. A silicone polymer of claim 1 wherein;
$R^4$ is alkyl having from 10 to 20 carbon atoms.

9. A silicone polymer of claim 1 wherein;
$R^3$ is

x, y and z are each independently integers ranging from 0 to 20, with the proviso that x+y+z is greater than 1.

10. A silicone polymer of claim 1 wherein;
$R^4$ is

x, y and z are each independently integers ranging from 0 to 20, with the proviso that x+y+z is greater than 1.

11. A silicone polymer of claim 1 wherein;
a is an integer from 50 to 2000.

12. A silicone polymer of claim 1 wherein;
a is an integer from 100 to 2000.

13. A silicone polymer of claim 1 wherein said catalyst is an alkyl amine conforming to the following structure:

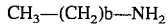

$CH_3-(CH_2)b-NH_2$ b is an integer ranging from 0 to 19.

14. A silicone polymer of claim 1 wherein said catalyst is an alkyl amine conforming to the following structure:

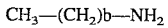

$CH_3-(CH_2)b-NH_2$ b is 6.

15. A silicone polymer of claim 3 wherein;
$R^3$ is alkyl having from 1 to 10 carbon atoms.

16. A silicone polymer of claim 3 wherein;
$R^3$ is alkyl having from 10 to 20 carbon atoms.

17. A silicone polymer of claim 3 wherein;
$R^4$ is alkyl having from 1 to 10 carbon atoms.

18. A silicone polymer of claim 3 wherein;
$R^4$ is alkyl having from 10 to 20 carbon atoms.

19. A silicone polymer of claim 3 wherein;
$R^3$ is

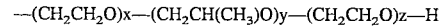

$-(CH_2CH_2O)x-(CH_2CH(CH_3)O)y-(CH_2CH_2O)z-H$ x, y and z are each independently integers ranging from 0 to 20, with the proviso that x+y+z is greater than 1.

20. A silicone polymer of claim 3 wherein;
$R^4$ is

$-(CH_2CH_2O)x-(CH_2CH(CH_3)O)y-(CH_2CH_2O)z-H$ x, y and z are each independently integers ranging from 0 to 20, with the proviso that x+y+z is greater than 1.

* * * * *